US012624157B2

(12) United States Patent
Miyatake et al.

(10) Patent No.: US 12,624,157 B2
(45) Date of Patent: May 12, 2026

(54) METHOD FOR PRODUCING ANION EXCHANGE RESIN AND METHOD FOR PRODUCING ELECTROLYTE MEMBRANE

(71) Applicants: UNIVERSITY OF YAMANASHI, Yamanashi (JP); TAKAHATA PRECISION CO., LTD., Tokyo (JP)

(72) Inventors: Kenji Miyatake, Yamanashi (JP); Yosuke Konno, Tokyo (JP); Naoki Yokota, Tokyo (JP); Katsuya Nagase, Tokyo (JP)

(73) Assignees: UNIVERSITY OF YAMANASHI, Yamanashi (JP); TAKAHATA PRECISION CO., LTD., Tokyo (JP)

( * ) Notice: Subject to any disclaimer, the term of this patent is extended or adjusted under 35 U.S.C. 154(b) by 632 days.

(21) Appl. No.: 18/003,781

(22) PCT Filed: Jul. 2, 2021

(86) PCT No.: PCT/JP2021/025062
§ 371 (c)(1),
(2) Date: Dec. 29, 2022

(87) PCT Pub. No.: WO2022/014356
PCT Pub. Date: Jan. 20, 2022

(65) Prior Publication Data
US 2023/0312813 A1 Oct. 5, 2023

(30) Foreign Application Priority Data
Jul. 16, 2020 (JP) ................................ 2020-121967

(51) Int. Cl.
*C07C 17/12* (2006.01)
*B01J 41/13* (2017.01)
(Continued)

(52) U.S. Cl.
CPC ............ *C08G 61/121* (2013.01); *C07C 17/12* (2013.01); *C07C 17/32* (2013.01); *C07C 209/08* (2013.01);
(Continued)

(58) Field of Classification Search
CPC ...... C08G 61/121; C08G 61/12; C08G 61/00; B01J 41/13
See application file for complete search history.

(56) References Cited

U.S. PATENT DOCUMENTS 10,287,409 B2 * 5/2019 Shimada et al. ....... C08J 5/2281
10,727,515 B2 * 7/2020 Miyatake et al. .. H01M 8/1023
(Continued)

FOREIGN PATENT DOCUMENTS

JP 2016-33199 A 3/2016
JP 2016-44224 A 4/2016
(Continued)

OTHER PUBLICATIONS

US 10,471,240 B2, 11/2019, Miyatake et al. (withdrawn)*
(Continued)

*Primary Examiner* — Rip A Lee
(74) *Attorney, Agent, or Firm* — MASUVALLEY & PARTNERS; Peter Martinez

(57) ABSTRACT

Provided are a method for producing an anion exchange resin which is capable of producing an electrolyte membrane with excellent mechanical property (strength).
A monomer for forming a hydrophobic group is reacted with a monomer for forming a hydrophilic group in the presence of bis(1,5-cyclooctadiene)nickel(0) as a catalyst, 2,2'-bipyridine as a co-ligand, a bromide or an iodide as a co-catalyst, and a reducing agent to produce an anion exchange resin where the hydrophobic group is connected to the hydrophilic group via direct bond, in which a mole number of bis(1,5-
(Continued)

cyclooctadiene)nickel(0) is 0.3 to 1.8 times a total mole number of the monomer for forming a hydrophobic group and the monomer for forming a hydrophilic group.

11 Claims, 1 Drawing Sheet

(51) Int. Cl.

| | |
|---|---|
| ***C07C 17/32*** | (2006.01) |
| ***C07C 209/08*** | (2006.01) |
| ***C08G 61/12*** | (2006.01) |
| ***C08J 5/22*** | (2006.01) |

(52) U.S. Cl.

CPC .............. *C08J 5/2262* (2013.01); *B01J 41/13* (2017.01); *C07C 2603/18* (2017.05); *C08G 2261/122* (2013.01); *C08G 2261/143* (2013.01); *C08G 2261/312* (2013.01); *C08G 2261/3142* (2013.01); *C08G 2261/3326* (2013.01); *C08G 2261/416* (2013.01); *C08G 2261/72* (2013.01); *C08J 2365/00* (2013.01)

(56) References Cited

U.S. PATENT DOCUMENTS

| | | | | |
|---|---|---|---|---|
| 10,734,663 | B2 * | 8/2020 | Miyatake et al. | .. H01M 8/1023 |
| 10,947,339 | B2 * | 3/2021 | Miyatake et al. | ..... C08G 61/12 |
| 11,154,852 | B2 * | 10/2021 | Miyatake et al. | ....... B01J 41/13 |
| 11,173,484 | B2 * | 11/2021 | Miyatake et al. | ....... B01J 41/13 |
| 2017/0267823 | A1 | 9/2017 | Shimada et al. | |
| 2018/0178210 | A1 | 6/2018 | Miyatake et al. | |
| 2018/0265626 | A1 | 9/2018 | Miyatake et al. | |
| 2019/0027767 | A1 | 1/2019 | Miyatake et al. | |
| 2019/0027768 | A1 | 1/2019 | Miyatake et al. | |

FOREIGN PATENT DOCUMENTS

| | | | |
|---|---|---|---|
| JP | 2017-14423 | A | 1/2017 |
| JP | 2017-61583 | A | 3/2017 |
| JP | 2019-23258 | A | 2/2019 |
| JP | 2019-23259 | A | 2/2019 |

OTHER PUBLICATIONS

WIPO, Japan International Search Authority, International Search Report with English Translation mailed Aug. 24, 2021 in International Patent Application No. PCT/JP2021/025062, 7 pages.

Ono, Hideaki et al. Robust anion conductive polymers containing perfluoroalkylene and pendant ammonium groups for high performance fuel cells. Journal of Materials Chemistry A. Dec. 21, 2017, vol. 5, No. 47, 24804-24812, scheme 1.

WIPO, Japan International Search Authority, Written Opinion mailed Aug. 24, 2021 in International Patent Application No. PCT/JP2021/025062, 3 pages.

* cited by examiner

METHOD FOR PRODUCING ANION EXCHANGE RESIN AND METHOD FOR PRODUCING ELECTROLYTE MEMBRANE

RELATED APPLICATIONS

This application is the U.S. National Phase of and claims priority to International Patent Application No. PCT/JP2021/025062, International Filing Date Jul. 2, 2021, entitled Method For Producing Anion Exchange Resin And Method For Producing Electrolyte Membrane; which claims priority to Japan Application No. 2020-121967 filed Jul. 16, 2020, both of which are incorporated herein by reference in their entireties.

TECHNICAL FIELD

The present invention relates to a method for producing an anion exchange resin and a method for producing an electrolyte membrane.

BACKGROUND ART

The anion exchange resin is known, in which the anion exchange resin comprises a divalent hydrophobic group being composed of a single aromatic ring, or being composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or carbon-carbon bond; and a divalent hydrophilic group being composed of a single polycyclic compound, or being composed of a plurality of polycyclic compounds which are connected to each other via a linking group and/or carbon-carbon bond, wherein the linking group is a divalent hydrocarbon group, a divalent silicon-containing group, a divalent nitrogen-containing group, a divalent phosphorus-containing group, a divalent oxygen-containing group, or a divalent sulfur-containing group; and at least one of the linking group or the polycyclic compound is connected to an anion exchange group via a divalent saturated hydrocarbon group with a carbon number of 2 or more; wherein the anion exchange resin comprises a hydrophobic unit being composed of the hydrophobic group alone, or being composed of a plurality of hydrophobic groups repeated via ether bond, thioether bond, or carbon-carbon bond; wherein the anion exchange resin comprises a hydrophilic unit being composed of the hydrophilic group alone, or being composed of a plurality of hydrophilic groups repeated via ether bond, thioether bond, or carbon-carbon bond; and wherein the hydrophobic unit and the hydrophilic unit are connected via ether bond, thioether bond, or carbon-carbon bond.

PRIOR ART DOCUMENT

Patent Document

Patent Document 1: JP 2019-23258 A

SUMMARY OF THE INVENTION

Problem to be Solved by the Invention

However, in the patent document 1, a large amount of bis(1,5-cyclooctadiene)nickel(0) which is very expensive is used as a catalyst the polymerization reaction (cross-coupling) of monomers to produce an anion exchange resin in which a hydrophobic unit and a hydrophilic unit are connected via carbon-carbon bond, which makes it difficult to reduce production cost. When the amount of the catalyst used is reduced, there is a problem that the molecular weight (in particular, weight average molecular weight) of the polymer obtained becomes lowered, which results in lowered mechanical property (strength) of the anion exchange resin.

Accordingly, an object of the present invention is to provide a method for producing an anion exchange resin which is capable of producing an electrolyte membrane with excellent mechanical property (strength) and a method for producing an electrolyte membrane formed from the anion exchange resin.

Means of Solving the Problem

In order to solve the above problem, a method for producing an anion exchange resin according to the present invention comprises:

(A) preparing a monomer for forming a hydrophobic group, being composed of a single aromatic ring or being composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond, wherein two chlorine atoms are bonded to the aromatic ring;

(B) preparing a monomer for forming a hydrophilic group, being composed of a single aromatic ring or being composed of a plurality of aromatic rings which are connected to each other via a linking group and/or via direct bond; wherein the linking group is a divalent hydrocarbon group, a divalent silicon-containing group, a divalent nitrogen-containing group, a divalent phosphorus-containing group, a divalent oxygen-containing group, or a divalent sulfur-containing group; two chlorine atoms are bonded to the aromatic ring; and at least one of the linking group or the aromatic ring is connected to a precursor functional group for an anion exchange group via a divalent saturated hydrocarbon group or direct bond;

(C) reacting the monomer for forming a hydrophobic group with the monomer for forming a hydrophilic group in the presence of bis(1,5-cyclooctadiene)nickel (0) as a catalyst, 2,2'-bipyridine as a co-ligand, a bromide or an iodide as a co-catalyst, and a reducing agent to synthesizing a polymer; and (D) ionizing the precursor functional group for an anion exchange group to form an anion exchange group;

wherein a mole number of bis(1,5-cyclooctadiene)nickel (0) used in the step (C) is 0.3 to 1.8 times a total mole number of the monomer for forming a hydrophobic group and the monomer for forming a hydrophilic group; and wherein, in the anion exchange resin, a residue of the monomer for forming a hydrophobic group forms a divalent hydrophobic group; a residue of the monomer for forming a hydrophilic group having the anion exchange group forms a divalent hydrophilic group; and the hydrophobic group is connected to the hydrophilic group via direct bond.

In the method of producing an anion exchange resin according to the present invention, it is suitable that the co-catalyst is a quaternary ammonium bromide or a quaternary ammonium iodide.

In the method of producing an anion exchange resin according to the present invention, it is suitable that a mole number of the co-catalyst used in the step (C) is 1.0 to 3.0 times the mole number of bis(1,5-cyclooctadiene)nickel(0).

In the method of producing an anion exchange resin according to the present invention, it is suitable that the reducing agent is metallic zinc or metallic magnesium.

In the method of producing an anion exchange resin according to the present invention, it is suitable that a mole number of 2,2'-bipyridine used in the step (C) is 1.5 to 2.5 times the mole number of bis(1,5-cyclooctadiene)nickel(0).

In the method of producing an anion exchange resin according to the present invention, it is suitable that the hydrophobic group comprises a bisphenol residue which may be substituted with a halogen atom, a pseudohalide, an alkyl group, or an aryl group, represented by the following formula (2).

(2)

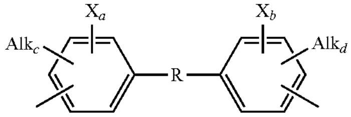

In the formula, R represents a hydrocarbon group, a silicon-containing group, a nitrogen-containing group, a phosphorus-containing group, an oxygen-containing group, a sulfur-containing group, or direct bond, which may be substituted with a halogen atom or a pseudohalide; Alk are the same or different from each other and each represents an alkyl group or an aryl group; X are the same or different from each other and each represents a halogen atom or a pseudohalide; and a, b, c, and d are the same or different from each other and each represents an integer of 0 to 4.

In the method of producing an anion exchange resin according to the present invention, it is suitable that the hydrophobic group comprises a bisphenol residue which may be substituted with a halogen atom, a pseudohalide, an alkyl group, or an aryl group, represented by the following formula (1) (in particular, Z are carbon atom, R are direct bond, X are fluorine atom, and h, h', h", i, i', i", j, and k are 0, in the following formula (1)).

(1)

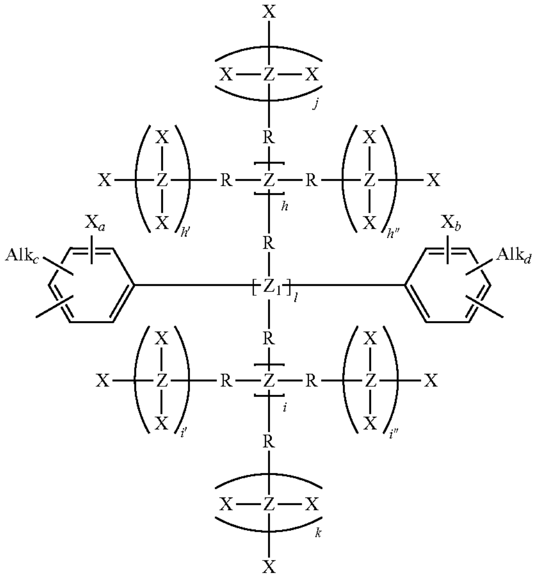

In the formula, Alk, X, a, b, c, and d respectively have the same meaning as Alk, X, a, b, c, and d in the formula (2); Z are the same or different from each other and each represents carbon atom or silicon atom; R are the same or different from each other and each represents a silicon-containing group, a nitrogen-containing group, a phosphorus-containing group, an oxygen-containing group, a sulfur-containing group, or direct bond; l represents an integer of 1 or more; and h, h', h", i, i', i", j, and k are the same or different from each other and each represents an integer of 0 or more.

In the method of producing an anion exchange resin according to the present invention, it is suitable that the hydrophilic group is a divalent hydrophilic group, being composed of a single polycyclic compound or being composed of a plurality of polycyclic compounds which are connected to each other via a linking group and/or via direct bond; wherein the linking group is a divalent hydrocarbon group, a divalent silicon-containing group, a divalent nitrogen-containing group, a divalent phosphorus-containing group, a divalent oxygen-containing group, or a divalent sulfur-containing group; and at least one of the linking group or the polycyclic compound is connected to an anion exchange group via a divalent saturated hydrocarbon group with a carbon number of 2 or more (in particular, the hydrophilic group comprises a fluorene residue represented by the following formula (3)).

(3)

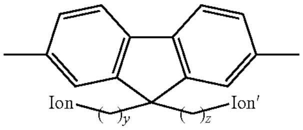

In the formula, Ion and Ion' are the same or different from each other and each represents an anion exchange group, and y and z are the same or different from each other and each represents an integer of 2 to 20.

In order to solve the above problem, a method for producing an electrolyte membrane comprises:

obtaining an anion exchange resin by the method described above; and obtaining an electrolyte membrane comprising the anion exchange resin.

Effect of the Invention

The present invention can provide a method for producing an anion exchange resin which is capable of producing an electrolyte membrane with excellent mechanical property (strength) and a method for producing an electrolyte membrane formed from the anion exchange resin.

MODE FOR CARRYING OUT THE INVENTION

Figure 1:
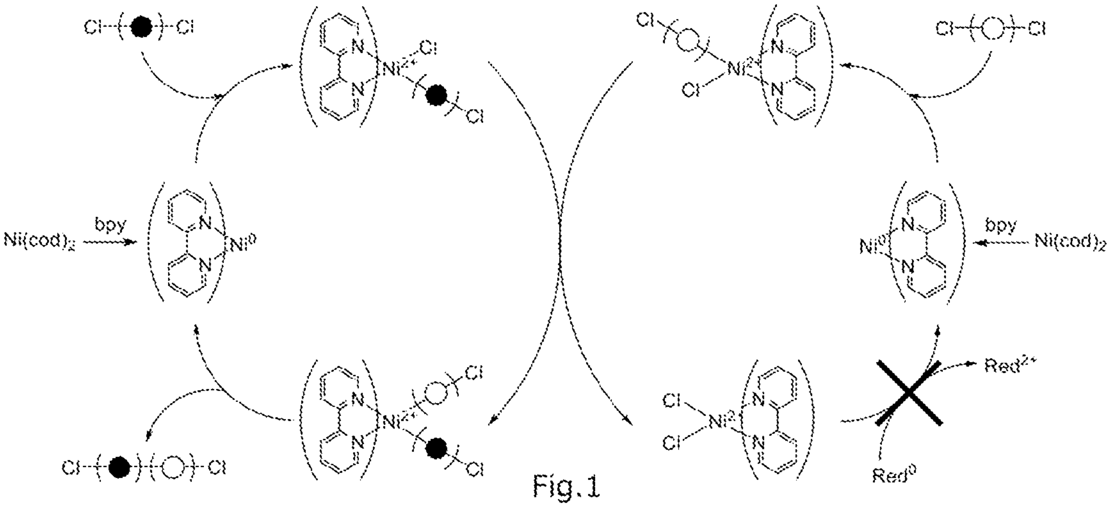
FIG. 1 shows the scheme of the cross-coupling reaction in the case where a co-catalyst is not used.

An anion exchange resin of the present invention consists of a divalent hydrophobic group and a divalent hydrophilic group.

In an anion exchange resin of the present invention, the divalent hydrophobic group is composed of a single aromatic ring or is composed of a plurality (two or more, preferably two) of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond (carbon-carbon bond). The divalent hydrophobic group is formed by a residue of a monomer for forming a hydrophobic group, which is composed of a single aromatic ring or is composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond, in which two halogen atoms, pseudohalides or boronic acid groups are bonded to the aromatic ring.

Examples of the aromatic ring include monocyclic or polycyclic compounds with a carbon number of 6 to 14 such as benzene ring, naphthalene ring, indene ring, azulene ring, fluorene ring, anthracene ring, and phenanthrene ring; and heterocyclic compounds such as azole, oxole, thiophene, oxazole, thiazole, and pyridine.

Preferred examples of the aromatic ring include monocyclic aromatic hydrocarbon with a carbon number of 6 to 14, and the aromatic ring is more preferably benzene ring.

The aromatic ring may be substituted with a substituent such as a halogen atom, an alkyl group, an aryl group, or a pseudohalide, as required. Examples of the halogen atom include fluorine atom, chlorine atom, bromine atom, and iodine atom. Examples of the pseudohalides include trifluoromethyl group, —CN, —NC, —OCN, —NCO, —ONC, —SCN, —NCS, —SeCN, —NCSe, —TeCN, —NCTe, and $—N_3$. Examples of the alkyl group include, for example, alkyl groups with a carbon number of 1 to 20 such as methyl group, ethyl group, propyl group, i-propyl group, butyl group, i-butyl group, sec-butyl group, t-butyl group, pentyl group, hexyl group, heptyl group, and octyl group; cycloalkyl groups with a carbon number of 1 to 20 carbons such as cyclopropyl group, cyclobutyl group, cyclopentyl group, cyclohexyl group, cycloheptyl group, and cyclooctyl group. Examples of the aryl group include, for example, phenyl group, biphenyl group, naphthyl group, and fluorenyl group.

In the case where the aromatic ring is substituted with a substituent such as a halogen atom, an alkyl group, an aryl group, or a pseudohalide, the substitute number and the substitute position of the substituent such as a halogen atom, an alkyl group, an aryl group, or a pseudohalide are appropriately set according to the purpose and the application.

The monomer for forming a hydrophobic group has at least two halogen atoms, pseudohalides, or boronic acid groups which are bonded to the aromatic ring. As for the bonding positions of the two halogen atoms, pseudohalides or boronic acid groups, in the case where the monomer for forming a hydrophobic group is composed of a single aromatic ring, they are the aromatic ring concerned; in the case where the monomer for forming a hydrophobic group has two aromatic rings, they are each of the aromatic rings; and in the case where the monomer for forming a hydrophobic group has three or more aromatic rings, they are aromatic rings at both ends.

The residue of the monomer for forming a hydrophobic group, excluding the two halogen atoms, pseudohalides or boronic acid groups bonded to the aromatic ring, forms a divalent hydrophobic group.

More specifically, examples of the aromatic ring substituted with a halogen atom include, for example, benzene rings substituted with 1 to 4 halogen atoms (for example, benzene rings substituted with 1 to 4 fluorine atoms, benzene rings substituted with 1 to 4 chlorine atoms, benzene rings substituted with 1 to 4 bromine atoms, benzene rings substituted with 1 to 4 iodine atoms, and the like; in which 1 to 4 halogen atoms may be all the same or different from each other).

Examples of the divalent hydrocarbon group include, for example, divalent saturated hydrocarbon groups with a carbon number of 1 to 20 such as methylene ($—CH_2—$), ethylene, propylene, i-propylene ($—C(CH_3)_2—$), butylene, i-butylene, sec-butylene, pentylene (pentene), i-pentylene, sec-pentylene, hexylene (hexamethylene), 3-methylpentene, heptylene, octylene, 2-ethylhexylene, nonylene, decylene, i-decylene, dodecylene, tetradecylene, hexadecylene, and octadecylene.

The divalent hydrocarbon group is preferably a saturated hydrocarbon group with a carbon number of 1 to 3. Specifically, examples include methylene ($—CH_2—$), ethylene, propylene, i-propylene ($—C(CH_3)_2—$), more preferred examples include methylene ($—CH_2—$) and isopropylene ($—C(CH_3)_2—$), and especially preferred examples include i-propylene ($—C(CH_3)_2—$).

The divalent hydrocarbon group may be substituted with a monovalent residue in the aromatic rings described above.

Examples of the aromatic group include, for example, divalent residues in the aromatic rings described above. Preferred examples include m-phenylene and fluorenyl group.

As the hydrophobic group, preferred examples include bisphenol residues which may be substituted with a halogen atom, a pseudohalide, an alkyl group, or an aryl group (divalent hydrophobic groups composed of two benzene rings which are connected to each other via R), represented by the following formula (2).

(2)

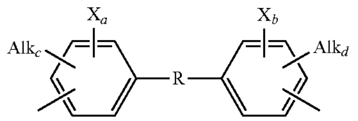

In the formula, R represents a hydrocarbon group, a silicon-containing group, a nitrogen-containing group, a phosphorus-containing group, an oxygen-containing group, a sulfur-containing group, an aromatic group, or direct bond; Alk are the same or different from each other and each represents an alkyl group or an aryl group; X are the same or different from each other and each represents a halogen atom or a pseudohalide; and a, b, c, and d are the same or different from each other and each represents an integer of 0 to 4.

In the above formula (2), R represents a hydrocarbon group, a silicon-containing group, a nitrogen-containing group, a phosphorus-containing group, an oxygen-containing group, a sulfur-containing group, or direct bond, and preferably represents i-propylene ($—C(CH_3)_2—$).

In the above formula (2), Alk are the same or different from each other and each represents an alkyl group or an aryl group. Examples of the alkyl group include the alkyl groups described above, and examples of the aryl group include the aryl group described above.

In the above formula (2), X are the same or different from each other and each represents a halogen atom or a pseudohalide, described above.

In the above formula (2), a and b are the same or different from each other and each represents an integer of 0 to 4, and preferably represents an integer of 0 to 2. Further preferably both a and b represent 0.

In the above formula (2), c and d are the same or different from each other and each represents an integer of 0 to 4, and preferably represents an integer of 0 to 2. Further preferably both c and d represent 0.

As the hydrophobic group, particularly preferred examples include bisphenol residues which may be substituted with a halogen atom, a pseudohalide, an alkyl group, or an aryl group, represented by the following formula (1).

(1)

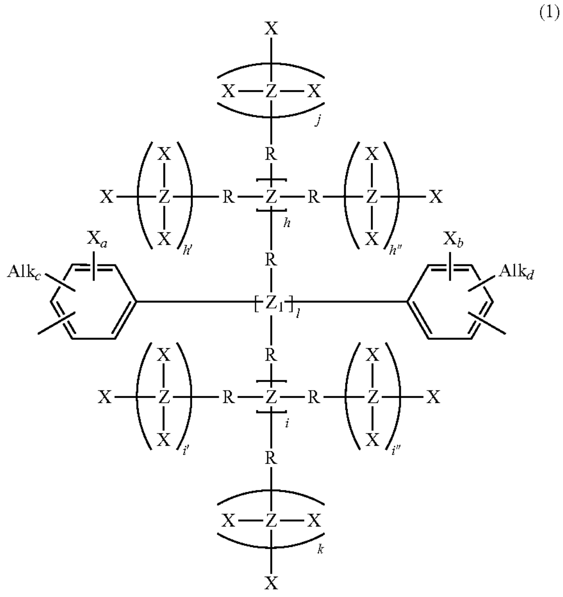

In the formula, Alk, X, a, b, c, and d respectively have the same meaning as Alk, X, a, b, c, and d in the formula (2); Z are the same or different from each other and each represents carbon atom or silicon atom; R are the same or different from each other and each represents a silicon-containing group, a nitrogen-containing group, a phosphorus-containing group, an oxygen-containing group, a sulfur-containing group, or direct bond; l represents an integer of 1 or more; and h, h', h", i, i', i", j, and k are the same or different from each other and each represents an integer of 0 or more.

In the above formula (1), Z are the same or different from each other and each represents carbon atom or silicon atom, and preferably represents carbon atom.

In the above formula (1), R are the same or different from each other and each represents a silicon-containing group, a nitrogen-containing group, a phosphorus-containing group, an oxygen-containing group, a sulfur-containing group, or direct bond, and preferably represents direct bond.

In the above formula (l), X are the same or different from each other and each represents a halogen atom, a pseudohalide, or hydrogen atom, described above, preferably represents a halogen atom or hydrogen atom, and more preferably represents fluorine atom.

In the above formula (1), l represents an integer of 1 or more, preferably represents an integer of 1 to 20, and more preferably represents an integer of 2 to 6.

In the above formula (l), h, h', h", i, i', i", j, and k are the same or different from each other and each represents an integer of 0 or more, preferably represents an integer of 0 to 20, more preferably represents an integer of 0 to 3, and furthermore preferably represents 0 or 1.

As the hydrophobic group, particularly preferred examples include fluorine-containing bisphenol residues represented by the following formula (1').

(1')

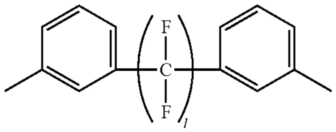

In the formula, l has the same meaning as l in the formula (1) described above.

Thus, by introducing a divalent fluorine-containing group into the main chain of the hydrophobic group, the following effects can be obtained.

The solubility and the flexibility are increased by the main chain having low intermolecular interaction.

The water repellency is provided, and ion conductive paths can be formed by the growing phase separation to a hydrophilic moiety (near the ion exchange group).

The water repellency prevents a hydrophilic hydroxide ion and an oxidant from accessing the main chain (providing improved alkali resistance and improved chemical stability).

The rigidity of the main chain can be controlled (providing improved flexibility of the electrolyte membrane).

It can adhere the catalyst layer due to its low glass transition temperature (providing decreased contact resistance).

The gas diffusion capability of the resin can be controlled (providing increased oxygen diffusion capability when used as a binder).

Preferred examples of the hydrophobic group include divalent hydrophobic groups composed of two or more aromatic rings which are connected to each other via direct bond, and specific examples thereof include linear oligophenylene groups represented by the following formula (2a).

(2a)

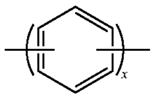

In the formula, x represents an integer of 2 to 8.

The electrical property (conductivity) becomes excellent by including a divalent hydrophobic group composed of two or more aromatic rings which are connected to each other via direct bond (preferably a linear oligophenylene group represented by the formula (2a) described above) as a hydrophobic group. In particular, even if the IEC (ion exchange capacity) is increased, the content number of water per one ionic group is not easily increased, which makes it easier to achieve high conductivity.

In the above formula (2a), x represents an integer of 2 to 8, preferably represents an integer of 2 to 6, and further preferably represents 2 (i.e., biphenylene group).

Other examples of the hydrophobic group include groups having the following structure.

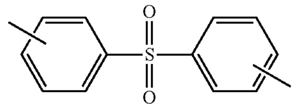
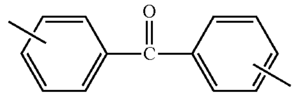
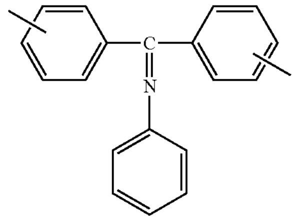
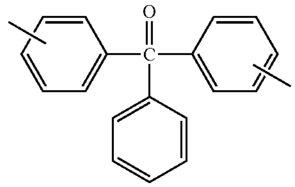
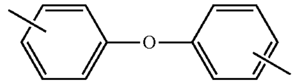
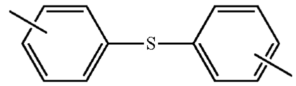
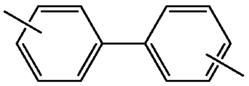
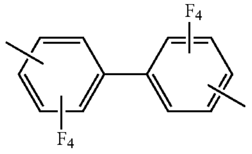

In an anion exchange resin of the present invention, the divalent hydrophilic group is composed of a single aromatic ring or is composed of a plurality of aromatic rings which are connected to each other via a linking group and/or via direct bond; in which the linking group is a divalent hydrocarbon group, a divalent silicon-containing group, a divalent nitrogen-containing group, a divalent phosphorus-containing group, a divalent oxygen-containing group, or a divalent sulfur-containing group; and in which at least one of the linking group or the aromatic ring is connected to an anion exchange group via a divalent saturated hydrocarbon group or direct bond. The divalent hydrophilic group is formed by a residue of a monomer for forming a hydrophilic group, which is composed of a single aromatic ring or is composed of a plurality of aromatic rings which are connected to each other via a linking group and/or via direct bond; in which the linking group is a divalent hydrocarbon group, a divalent silicon-containing group, a divalent nitrogen-containing group, a divalent phosphorus-containing group, a divalent oxygen-containing group, or a divalent sulfur-containing group; in which two halogen atoms, pseudohalides or boronic acid groups are bonded to the aromatic ring; and in which at least one of the linking group or the aromatic ring is connected to a precursor functional group for an anion exchange group via a divalent saturated hydrocarbon group or direct bond.

Examples of the aromatic ring include, for example, aromatic rings described above, and the aromatic ring is preferably benzene ring.

Preferred examples of the aromatic ring include polycyclic compounds. Examples of the polycyclic compound include naphthalene ring, indene ring, azulene ring, fluorene ring, anthracene ring, phenanthrene ring, carbazole ring, and indole ring, and preferred examples include fluorene ring.

Examples of the divalent hydrocarbon group include divalent hydrocarbon groups described above.

The anion exchange group is introduced into the side chain in the hydrophilic group. Specifically, the anion exchange group is not particularly limited, and any known anion exchange groups such as quaternary ammonium groups, tertiary amino groups, secondary amino groups, primary amino groups, phosphine, phosphazene, tertiary sulfonium groups, quaternary boronium groups, quaternary phosphonium groups, and guanidinium group can be selected as the anion exchange group. From the viewpoint of the anion conductivity, preferred examples of the anion exchange group include quaternary ammonium groups.

Preferred examples of the anion exchange group include —$N^+(CH_3)_3$. Other examples of the anion exchange group include groups having the following structures. In the following structural formulae, * represents a moiety bonded to the aromatic ring having a substituent group.

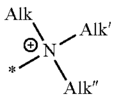
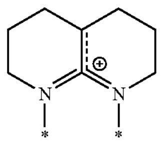
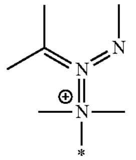
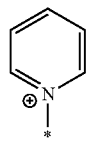
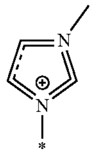
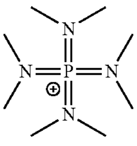
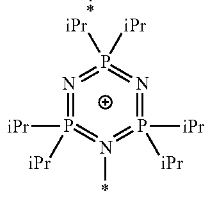

In the figure, Alk, Alk', and Alk" represent an alkyl group described above, and iPr represents i-propyl group).

The anion exchange group is connected to the linking group or the aromatic ring of the divalent hydrophilic residue via a divalent saturated hydrocarbon group or direct bond, in which the divalent hydrophilic residue is composed of a plurality of aromatic rings which are connected to each other via a linking group and/or direct bond, and in which the linking group is a divalent hydrocarbon group, a divalent silicon-containing group, a divalent nitrogen-containing group, a divalent phosphorus-containing group, a divalent oxygen-containing group, or a divalent sulfur-containing group.

The anion exchange group need only be connected to at least one of the linking group or the aromatic ring. The anion exchange group may be connected to a plurality of linking groups or aromatic rings, and may be connected to all linking groups or aromatic rings. A plurality of anion exchange groups may be connected to one linking group or aromatic ring.

The carbon number of the divalent saturated hydrocarbon group for connecting the anion exchange group to the linking group or the aromatic ring of the divalent hydrophilic residue is preferably 2 or more, in which the divalent hydrophilic residue is composed of a plurality of aromatic rings which are connected to each other via the linking group and/or direct bond, and in which the linking group is a divalent hydrocarbon group, a divalent silicon-containing group, a divalent nitrogen-containing group, a divalent phosphorus-containing group, a divalent oxygen-containing group, or a divalent sulfur-containing group. The carbon number of the divalent saturated hydrocarbon group is more preferably an integer of 2 to 20, is further preferably an integer of 3 to 10, and is particularly preferably an integer of 4 to 8.

Preferred examples of the divalent saturated hydrocarbon group include linear saturated hydrocarbon groups such as ethylene ($-(CH_2)_2-$), trimethylene ($-(CH_2)_3-$), tetramethylene ($-(CH_2)_4-$), pentamethylene ($-(CH_2)_5-$), hexamethylene ($-(CH_2)_6-$), heptamethylene ($-(CH_2)_7-$), and octamethylene ($-(CH_2)_8-$).

Preferred examples of the hydrophilic group include fluorene residues represented by the following formula (3).

(3)

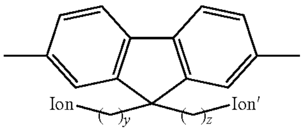

In the formula, Ion and Ion' are the same or different from each other and each represents an anion exchange group, and y and z are the same or different from each other and each represents an integer of 2 to 20.

In the above formula (3), Ion and Ion' are the same or different from each other and each represents an anion exchange group. Preferably, Ion and Ion' are the same or different from each other and each represents a quaternary ammonium group described above. Particularly preferably, Ion and Ion' are $-N^+(CH_3)_3$.

In the above formula (3), y and z are the same or different from each other and each represents an integer of 2 to 20, preferably represents an integer of 3 to 10, and further preferably represents an integer of 4 to 8.

Particularly preferred examples of the hydrophilic group include fluorene residues represented by the following formula (3').

(3')

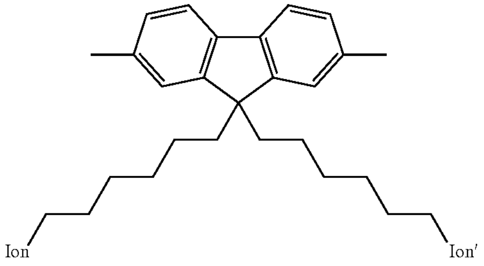

In an anion exchange resin of the present invention, the hydrophobic group described above and the hydrophilic group described above are bonded via direct bond. In an anion exchange resin of the present invention, the hydrophobic groups described above are preferably repeated via ether bond, thioether bond, or direct bond to form a hydrophobic unit. In an anion exchange resin of the present invention, the hydrophilic groups described above are preferably repeated via ether bond, thioether bond, or direct bond to form a hydrophilic unit. Hereinafter, the hydrophobic unit is those composed of a single hydrophobic group or those composed of hydrophobic groups repeated via direct bond, while the hydrophilic unit is those composed of a single hydrophilic group or those composed of hydrophilic groups repeated via direct bond.

The unit may correspond to a block of a block copolymer as generally used.

Preferred examples of the hydrophobic unit include units formed by bisphenol residues which may be substituted with an alkyl group, an aryl group, a halogen atom, or a pseudohalide, represented by the formula (2) described above, in which the bisphenol residues are connected to each other via direct bond. The bisphenol residue described above may also be a unit formed by multiple species connected to each other in random form, in ordered form including alternating, or in block form.

For example, the hydrophobic unit is represented by the following formula (7).

(7)

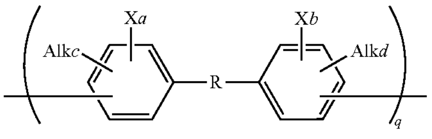

In the formula, R, Al, X, a, b, c, and d respectively have the same meaning as R, Al, X, a, b, c, and d in the formula (2) described above; and q represents 1 to 200.

In the above formula (7), q represents 1 to 200, for example. Preferably, q represents 1 to 50.

Further preferred examples of the hydrophobic unit include units formed by bisphenol residues which may be substituted with a halogen atom, a pseudohalide, an alkyl group, or an aryl group, represented by the formula (1) described above, in which the bisphenol residues are connected to each other via direct bond.

For example, the hydrophobic unit is represented by the following formula (7a).

(7a)

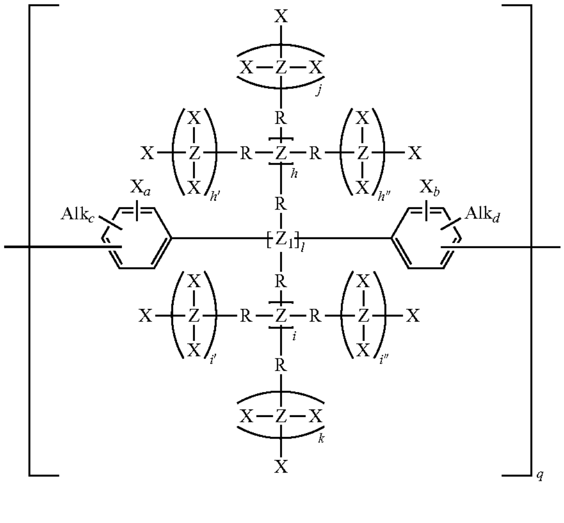

In the formula, Alk, X, a, b, c, and d respectively have the same meaning as Alk, X, a, b, c, and d in the formula (2) described above; Z, R, X, l, h, h', h", i, i', i", j, and k respectively have the same meaning as Z, R, X, l, h, h', h", i, i', i", j, and k in the formula (1) described above; and q represents 1 to 200.

In the above formula (7), q represents 1 to 200, for example. Preferably, q represents 1 to 50.

Particularly preferably, the hydrophobic unit is represented by the following formula (7a').

(7a')

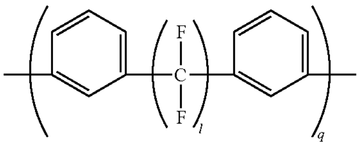

In the formula, l has the same meaning as l in the formula (1) described above; and q represents 1 to 200 (preferably, 1 to 50).

Preferred examples of the hydrophilic unit include units formed by fluorene residues (hydrophilic groups) represented by the formula (3) described above in which the fluorene residues are connected to each other via ether bond, thioether bond, or direct bond (preferably, direct bond). The fluorene residue described above may also be a unit formed by multiple species connected to each other in random form, in ordered form including alternating, or in block form.

For example, the hydrophilic unit is represented by the following formula (9').

(9')

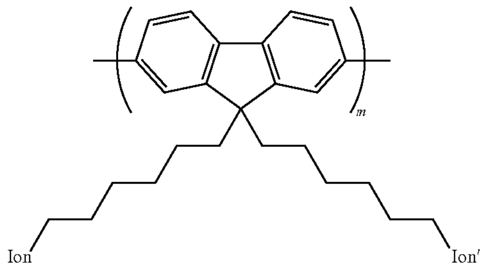

In the formula, Ion and Ion' are the same or different from each other and respectively have the same meaning as Ion and Ion' in the formula (3) described above; and m represents 1 to 200 (preferably, 1 to 50).

In an anion exchange resin of the present invention, it is preferable that the hydrophobic unit described above and the hydrophilic unit described above are connected via direct bond.

Preferred examples of the anion exchange resin include anion exchange resins obtained by connecting the hydrophobic unit represented by the formula (7) described above and the hydrophilic unit represented by the formula (9) described above via direct bond, which is represented by the following formula (13).

(13)

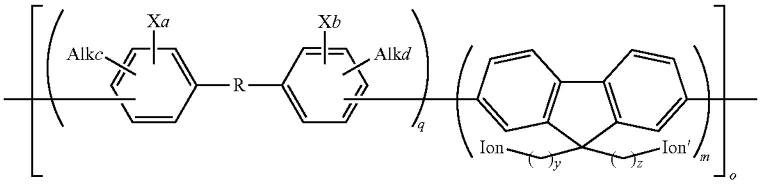

For example, the hydrophilic unit is represented by the following formula (9).

(9)

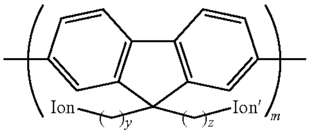

In the formula, Ion, Ion', y, and z are the same or different from each other and respectively have the same meaning as Ion, Ion', y, and z in the formula (3) described above; and m represents 1 to 200 (preferably, 1 to 50).

Further preferred examples of the hydrophilic unit include units formed by fluorene residues represented by the formula (3') described above, in which the fluorene residues are connected to each other via direct bond.

In the formula, R, Al, X, a, b, c, and d respectively have the same meaning as R, Al, X, a, b, c, and d in the formula (7) described above; Ion, Ion', y, and z respectively have the same meaning as Ion, Ion', y, and z in the formula (9) described above; q and m are a blending ratio or a repeating number and each represent 1 to 100; and o is a repeating number and represents 1 to 100.

Further preferred examples of the anion exchange resin include anion exchange resins obtained by connecting the hydrophobic unit represented by the formula (7a) described above and the hydrophilic unit represented by the formula (9) described above via direct bond, which is represented by the following formula (13').

(13')

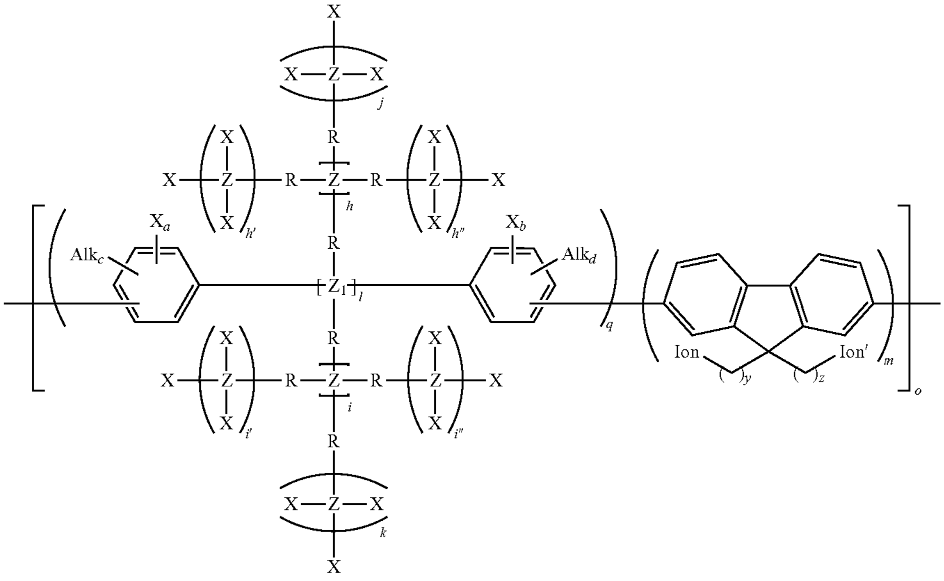

Particularly preferred examples of the anion exchange resin include anion exchange resins obtained by connecting the hydrophobic unit represented by the formula (7a') described above and the hydrophilic unit represented by the formula (9') described above via direct bond, which is represented by the following formula (13").

(13")

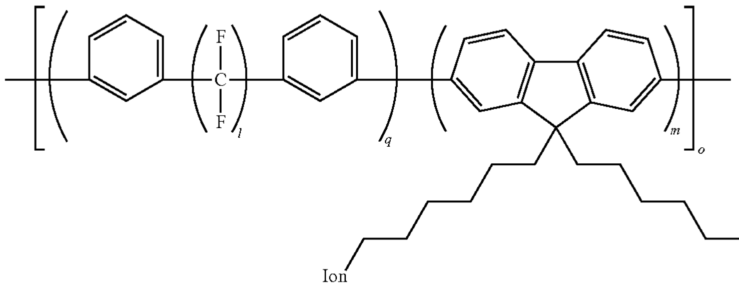

In the formula, l has the same meaning as l in the formula (7a') described above; Ion and Ion' respectively have the same meaning as Ion and Ion' in the formula (9') described above; q and m are a blending ratio or a repeating number and each represent 1 to 100; and o is a repeating number and represents 1 to 100.

The number average molecular weight of the anion exchange resin is, for example, 10 to 1000 kDa, and is preferably 30 to 500 kDa; and the weight average molecular weight is, for example, 20 to 3000 kDa, and is preferably 40 to 1000 kDa.

As a method for producing an anion exchange resin, a method by polycondensation reaction is adopted, and cross-coupling to form direct bond (carbon-carbon bond) is especially adopted.

In the case where an anion exchange resin is produced by the method, the anion exchange resin can be produced by preparing a monomer for forming a hydrophobic group, by preparing a monomer for forming a hydrophilic group having a precursor functional group for an anion exchange group, by polymerizing the monomer for forming a hydrophobic group and the monomer for forming a hydrophilic group to form a polymer, and by ionizing the precursor functional group for an anion exchange group in the polymer.

Examples of the monomer for forming a hydrophobic group include those being composed of a single aromatic ring or being composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond, in which two chlorine atoms are bonded to the aromatic ring. Preferred examples include compounds represented by the following formula (22), which corresponds to the formula (2) described above.

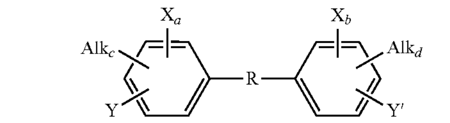

(22)

In the formula, Alk, R, X, a, b, c, and d respectively have the same meaning as Alk, R, X, a, b, c, and d in the formula (2) described above; Y and Y' are the same or different from each other and each represents chlorine atom.

Particularly preferred examples of the monomer for forming a hydrophobic group include compounds represented by the following formula (21), which corresponds to the formula (1) described above.

(21)

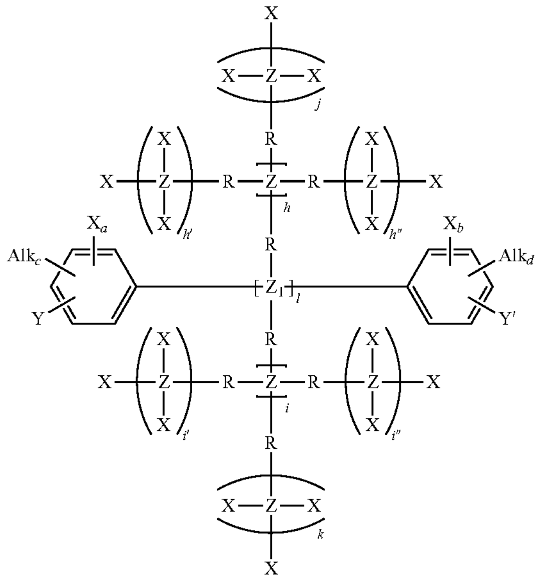

In the formula, Alk, R, X, Z, a, b, c, d, l, h, h', h'', i, i', i'', j, and k respectively have the same meaning as Alk, R, X, Z, a, b, c, d, l, h, h', h'', i, i', i'', j, and k in the formula (1) described above; Y and Y' are the same or different from each other and each represents chlorine atom.

Examples of the monomer for forming a hydrophilic group monomer include those being composed of a single aromatic ring or being composed of a plurality of aromatic rings which are connected to each other via a linking group and/or via direct bond; in which the linking group is a divalent hydrocarbon group, a divalent silicon-containing group, a divalent nitrogen-containing group, a divalent phosphorus-containing group, a divalent oxygen-containing group, or a divalent sulfur-containing group; in which two chlorine atoms are bonded to the aromatic ring; and in which at least one of the linking group or the aromatic ring is connected to a precursor functional group for an anion exchange group via a divalent saturated hydrocarbon group or direct bond. Preferred examples include compounds represented by the following formula (23), which corresponds to the formula (3) described above.

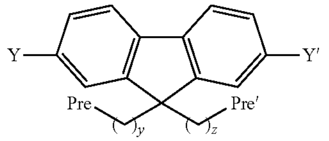

(23)

In the formula, y and z respectively have the same meaning as y and z in the formula (3) described above; Pre and Pre' are the same or different from each other and each represents a precursor functional group for an anion exchange group; and Y and Y' are the same or different from each other and each represents chlorine atom.

In polymerizing the monomer for forming a hydrophobic group with the monomer for forming a hydrophilic group by cross-coupling, the blending amount of each monomer is respectively adjusted so as to achieve a desired blending ratio of the hydrophobic unit and the hydrophilic unit in the resulting anion exchange resin precursor polymer.

In the present invention, the monomer for forming a hydrophobic group and the monomer for forming a hydrophilic group are dissolved in a solvent such as N,N-dimethylacetamide or dimethyl sulfoxide, for example; and the polymerization is carried out with bis(cycloocta-1,5-diene) nickel(0) (hereinafter sometimes referred to as "$Ni(cod)_2$") as a catalyst. When carrying out the cross-coupling reaction in a presence of bis(cycloocta-1,5-diene)nickel(0) as a catalyst, 2,2'-bipyridine (hereinafter sometimes referred to as "bpy") is present as a co-ligand.

Here, the scheme of the cross-coupling reaction described above is shown in FIG. 1. The cross-coupling reaction proceeds while $Ni(cod)_2$ that is a catalyst is consumed. If Ni of $Ni(bpy)Cl_2$ that is a consumed catalyst can be reduced with a reducing agent ($Red^0$), the entire reaction cycle will be established, and very expensive $Ni(cod)_2$ used can be reduced. However, it is difficult that Ni of $Ni(bpy)Cl_2$ that is a consumed catalyst is reduced with a common reducing agent.

Figure 2:
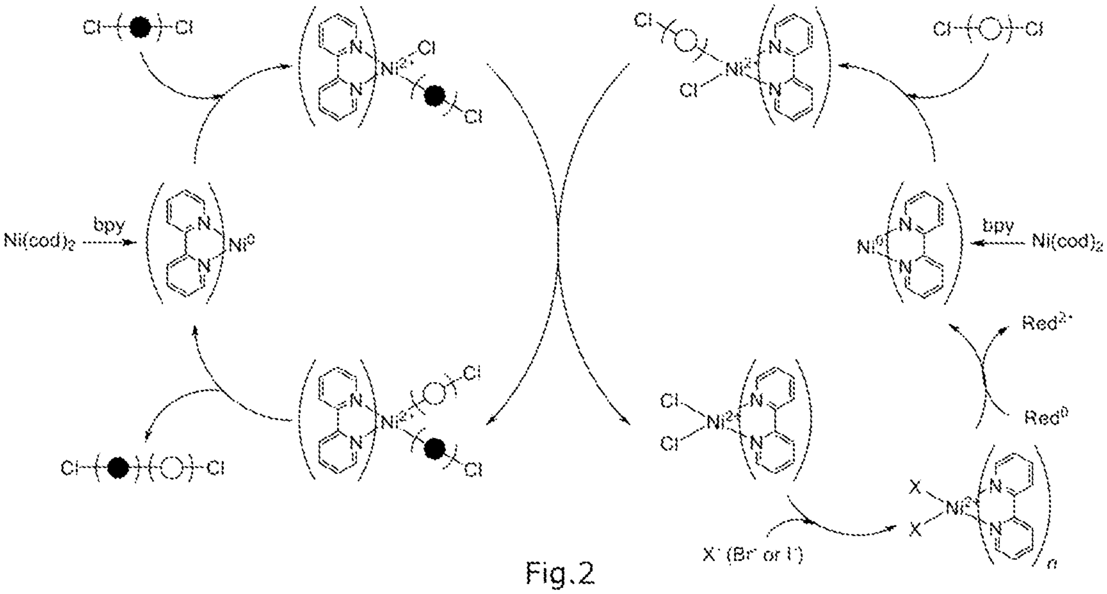
FIG. 2 shows the scheme of the cross-coupling reaction in the case where a co-catalyst is used.

Therefore, in the present invention, a bromide or an iodide as a co-catalyst and a reducing agent are coexisted in the cross-coupling reaction described above. The scheme of the cross-coupling reaction is shown in FIG. 2, in the case where a bromide or an iodide as a co-catalyst and a reducing agent are coexisted. The chlorine ions of the consumed catalyst residue ($Ni(bpy)Cl_2$) are once replaced by bromine ions or iodine ions by the co-catalyst, and the replaced catalyst residue can be reduced by a common reducing agent, which can establish an overall reaction cycle. Thus, very expensive $Ni(cod)_2$ used can be reduced and the production cost can be easily lowered.

In the present invention, the mole number of bis(1,5-cyclooctadiene)nickel(0) used as a catalyst can be 0.3 to 1.8 times the total mole number of the monomer for forming a hydrophobic group and the monomer for forming a hydrophilic group, can be preferably 0.4 to 1.5 times, and can be more preferably 0.5 to 1.0 times. In this case, the mole number of 2,2'-bipyridine used as a co-ligand is preferably 1.5 to 2.5 times the mole number of bis(1,5-cyclooctadiene) nickel(0) used as a catalyst, and is more preferably 1.8 to 2.2 times. In this way, the molecular weight of the resulting polymer can be increased and the mechanical property (strength) of the anion exchange resin can be improved.

As the co-catalyst, a bromide or an iodide can be used, and a quaternary ammonium bromide or a quaternary ammonium iodide can more preferably be used. Examples of the quaternary ammonium bromide include tetramethylammonium bromide, tetraethylammonium bromide, and tetrabutylammonium bromide. Examples of the quaternary ammonium iodide include tetramethylammonium iodide, tetraethylammonium iodide, and tetrabutylammonium iodide. The mole number of the co-catalyst used in the cross-coupling reaction described above is preferably 1.0 to 3.0 times the mole number of bis(1,5-cyclooctadiene)nickel (0), and is more preferably 1.5 to 2.5 times.

For example, metallic zinc or metallic magnesium can be used as a reducing agent. The mole number of the reducing agent used in the cross-coupling reaction described above is preferably 1.0 to 3.0 times the mole number of the co-catalyst, and is more preferably 1.5 to 2.5 times.

The reaction temperature in the cross-coupling reaction is, for example, −100 to 300° C., is preferably −50 to 200° C. The reaction time is, for example, 1 to 48 hours, and is preferably 2 to 5 hours.

By this reaction, an anion exchange resin precursor polymer represented by the following formula (15) and the following formula (16).

In the formula, Alk, R, X, Z, a, b, c, d, l, h, h', h", i, i', i", j, and k respectively have the same meaning as Alk, R, X, Z, a, b, c, d, l, h, h', h", i, i', i", j, and k in the formula (1) described above; y and z respectively have the same meaning as y and z in the formula (3) described above; Pre and Pre' are the same or different from each other and each represents a precursor functional group for an anion exchange group; q and m are a blending ratio or a repeating number and each represent 1 to 100; and o is a repeating number and represents 1 to 100.

In this method, the precursor functional group for an anion exchange group is then ionized. The method of ionization is not limited and any known method can be adopted.

For example, the anion exchange resin precursor polymer can be dissolved in a solvent such as N,N-dimethylacetamide or dimethyl sulfoxide and can be ionized using methyl iodide or the like as an alkylating agent, and any other known method can be adopted.

(15)

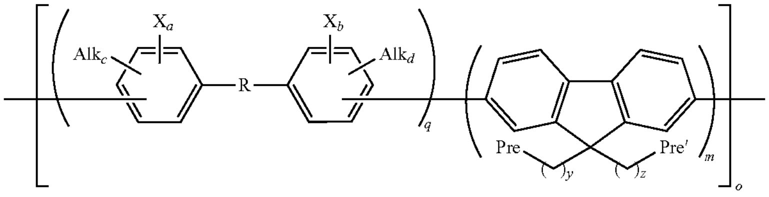

In the formula, Alk, R, X, a, b, c, and d respectively have the same meaning as Alk, R, X, a, b, c, and d in the formula (1) described above; y and z respectively have the same meaning as y and z in the formula (3) described above; Pre and Pre' are the same or different from each other and each represents a precursor functional group for an anion exchange group; q and m are a blending ratio or a repeating number and each represent 1 to 100; and o is a repeating number and represents 1 to 100.

The reaction temperature in the ionization reaction is, for example, 0 to 100° C., and is preferably 20 to 80° C. The reaction time is, for example, 24 to 72 hours, and is preferably 48 to 72 hours.

By this reaction, an anion exchange resin represented by the formulae (13) and (13') described above.

The ion exchange capacity of the anion exchange resin is, for example, 0.1 to 4.0 meq./g, and is preferably 0.6 to 3.0 meq./g.

(16)

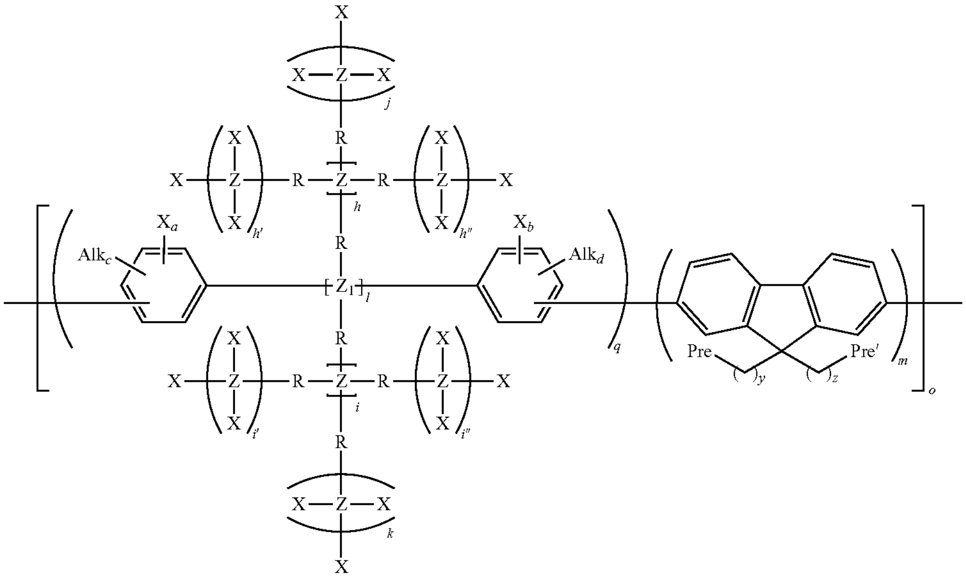

The ion exchange capacity can be calculated by the following equation (24).

[ion exchange capacity (meq./g)]=the amount of the anion exchange group introduced per hydrophilic unit×the repeating number of the hydrophilic unit×1000/(the molecular weight of the hydrophobic unit×the repeating number of the hydrophobic unit+the molecular weight of the hydrophilic unit×the repeating unit number of the hydrophilic unit+the molecular weight of the ion exchange group×the repeating unit number of the hydrophilic unit) (24)

The amount of the ion exchange group introduced is defined as the number of the ion exchange group per unit of the hydrophilic group. The amount of the anion exchange group introduced is the mole number (mol) of the an anion exchange group introduced in the main chain or the side chain of the hydrophilic group.

In the anion exchange resin, a hydrophobic group is connected to a hydrophilic group via direct bond; in which the hydrophobic group is composed of a single aromatic ring or is composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond; in which the hydrophilic group is composed of a single aromatic ring or is composed of a plurality of aromatic rings which are connected to each other via a linking group and/or via direct bond; in which the linking group is a divalent hydrocarbon group, a divalent silicon-containing group, a divalent nitrogen-containing group, a divalent phosphorus-containing group, a divalent oxygen-containing group, or a divalent sulfur-containing group; and in which at least one of the linking group or the aromatic ring is connected to an anion exchange group via a divalent saturated hydrocarbon group or direct bond. The anion exchange resin has excellent mechanical property (strength).

In addition, in the case where the anion exchange resin has a hydrophilic unit being composed of hydrophilic groups repeated via direct bond, the hydrophilic unit does not have ether bond, and therefore the anion exchange resin has improved durability such as alkali resistance. More specifically, if the hydrophilic unit has ether bond, the decomposition by hydroxide ion ($OH^-$) as described below may occur, and alkali resistance may not be sufficient.

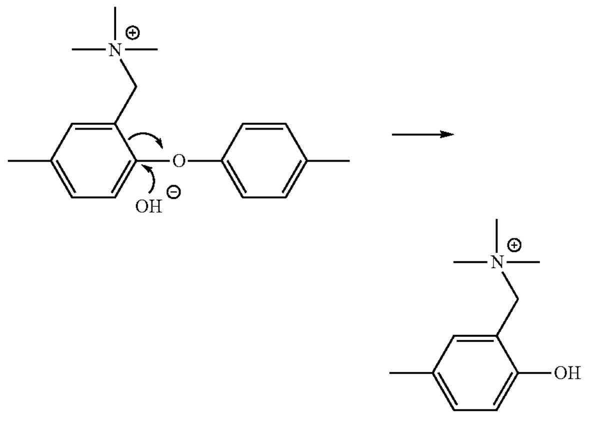

In contrast, since the hydrophilic unit of the anion exchange resin having a hydrophilic unit being composed of the hydrophilic groups repeated via direct bond does not have ether bond, the decomposition by the mechanism described above does not occur, and therefore the anion exchange resin has an improved durability such as alkali resistance.

The present invention includes electrolyte layers (electrolyte membranes) obtained by using the anion exchange resin. An electrolyte membrane of the present invention is applicable to various electrochemical applications such as fuel cells, water electrolysis devices, and electrochemical hydrogen pumps, but is particularly suitable for use in water electrolysis devices. In fuel cells, electrochemical hydrogen pumps, and water electrolysis hydrogen generators, the electrolyte membrane is used in a structural state in which catalyst layers, electrode substrates, and separators are sequentially laminated on both sides. Among these, the structure material with catalyst layers and gas diffusion substrates sequentially laminated on both sides of the electrolyte membrane (with layer composition of gas diffusion substrate/catalyst layer/electrolyte membrane/catalyst layer/gas diffusion substrate) is called membrane electrode Assembly (MEA). An electrolyte membrane of the present invention is suitably used as an electrolyte membrane that constitutes an MEA.

The anion exchange resin described above can be used as an electrolyte membrane (i.e., the electrolyte membrane contains the anion exchange resin described above).

The electrolyte membrane can be reinforced, for example, with a known reinforcing material such as a porous substrate, and can also be subjected to various treatments such as biaxial stretching treatments to control the molecular orientation and heat treatments to control crystallinity and residual stress. Known fillers can be added to the electrolyte membrane to increase the mechanical strength, and the electrolyte membrane can be composited with a reinforcing agent such as a glass nonwoven fabric by pressing.

In addition, various additives normally used in electrolyte membranes, such as compatibilizers to improve the compatibility, antioxidants to prevent the resin degradation, antistatic agents and lubricants to improve the handling during the film forming and processing, may be included as needed to the extent that they do not affect processing and performance as an electrolyte membrane.

The thickness of the electrolyte membrane is not particularly limited and is suitably set according to the purpose and application.

The thickness of the electrolyte membrane is, for example, 0.1 to 350 μm, and is preferably 1 to 200 μm.

Although the embodiments of the present invention have been described hereinabove, embodiments of the present invention are not limited to the embodiments, but may be modified as appropriate to the extent which does not change the scope of the invention.

EXAMPLE

The present invention is described based on the Examples and the Comparative Examples, but the present invention is not limited to the following Examples.

<Synthesis of Monomer 1>

To a 100 mL round-shaped three-necked flask equipped with a nitrogen inlet and a condenser were added 1,6-diiodoperfluorohexane (5.54 g, 10.0 mmol), 3-chloroiodobenzene (11.9 g, 50 mmol), and N,N-dimethyl sulfoxide (60 mL). After the mixture was stirred to form a homogeneous solution, copper powder (9.53 g, 150 mmol) was added, and the reaction was carried out at 120° C. for 48 hours. The reaction was quenched by adding the reaction solution dropwise to 0.1 M aqueous nitric acid solution. The mixture was filtered to collect the precipitate. The precipitate was washed with methanol, and then the filtrate was collected. After the similar procedure was repeated, a white solid was precipitated by adding pure water to the combined filtrate. The white solid was filtered and collected, was washed with a mixed solution of pure water and methanol (pure water/methanol=1/1), and was then dried under vacuum overnight (60° C.) to obtain a monomer 1 (white solid) represented by the following formula in a yield of 84%.

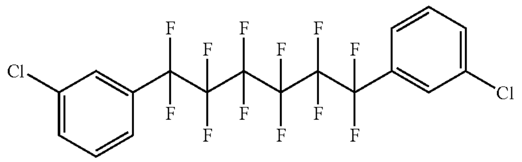 [SMILES: FC(F)(c1cccc(Cl)c1)C(F)(F)C(F)(F)C(F)(F)C(F)(F)C(F)(F)c1cccc(Cl)c1]

<Synthesis of Monomer 2>

To a 500 mL round-shaped three-necked flask were added fluorene (83.1 g, 0.50 mol), N-chlorosuccinimide (167 g, 1.25 mol), and acetonitrile (166 mL). After the mixture was stirred to form a homogeneous solution, 12 M hydrochloric acid (16.6 mL) was added, and the reaction was carried out at room temperature for 24 hours. The reaction mixture was filtered to collect the precipitate. The precipitate was washed with methanol and with pure water, and was then dried under vacuum overnight (60° C.) to obtain a monomer 2 (white solid) represented by the following formula in a yield of 65%.

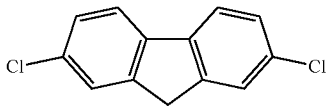 [SMILES: Clc1ccc2c(c1)Cc1cc(Cl)ccc1-2]

<Synthesis of Monomer 3>

To a 300 mL round-shaped three-necked flask were added the monomer 2 (8.23 g, 35.0 mmol) and 1,6-dibromohexane (53 mL). After the mixture was stirred to form a homogeneous solution, a mixed solution of tetrabutylammonium (2.26 g, 7.00 mmol), potassium hydroxide (35.0 g), and pure water (35 mL) were added, and the reaction was carried out at 80° C. for 1 hour. The reaction was quenched by adding pure water to the reaction solution. The target compound was extracted with dichloromethane from the water layer. The combined organic layer was washed with pure water and with sodium chloride solution, and then water, dichloromethane, and 1,6-dibromohexane were distilled off. The crude product was purified by column chromatography on silica gel (eluent: dichlorometane/hexane=1/4), and was then dried under vacuum overnight (60° C.) to obtain a monomer 3 (pale yellow solid) represented by the following formula in a yield of 75%.

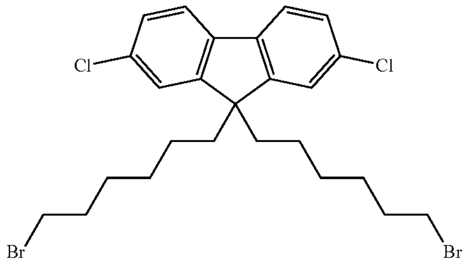 [SMILES: Clc1ccc2c(c1)C(CCCCCCBr)(CCCCCCBr)c1cc(Cl)ccc1-2]

<Synthesis of Monomer 4>

To a 300 mL round-shaped three-necked flask were added the monomer 3 (13.2 g, 23.4 mol) and tetrahydrofuran (117 mL). After the mixture was stirred to form a homogeneous solution, 40 wt % dimethylamine aqueous solution (58.6 mL) was added, and the reaction was carried out at room temperature for 24 hours. The reaction was quenched by adding a saturated solution of sodium hydrogen carbonate in water to the reaction solution. Tetrahydrofuran was removed from the solution and then the target ingredient was extracted by adding hexane. The organic layer was washed with sodium chloride solution, and then water and hexane were distilled off. The resulting product was dried under vacuum overnight at 40° C. to obtain a monomer 4 (pale yellow solid) represented by the following formula in a yield of 75%.

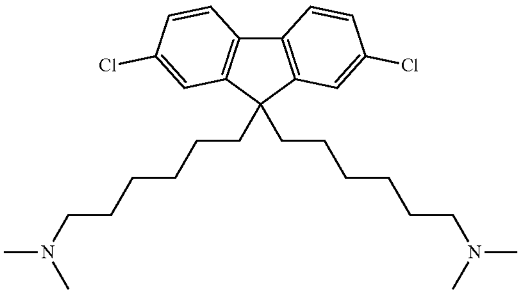

Example 1 Synthesis of Anion Exchange Resin 1

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 0.496 g, 3.14 mmol, 1.2 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 0.432 g, 1.57 mmol, 0.6 eq.), and the reaction was carried out at 80° C. for 1 hour. To the resulting slurry was added tetraethylammonium iodide (TEAI, 0.807 g, 3.14 mmol, 1.2 eq.) as a co-catalyst and zinc (Zn, 0.411 g, 6.28 mmol, 2.4 eq.) as a reducing agent, and the reaction was carried out at 80° C. for 2 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer 1 (yellow solid) represented by the following formula in a yield of 96%.

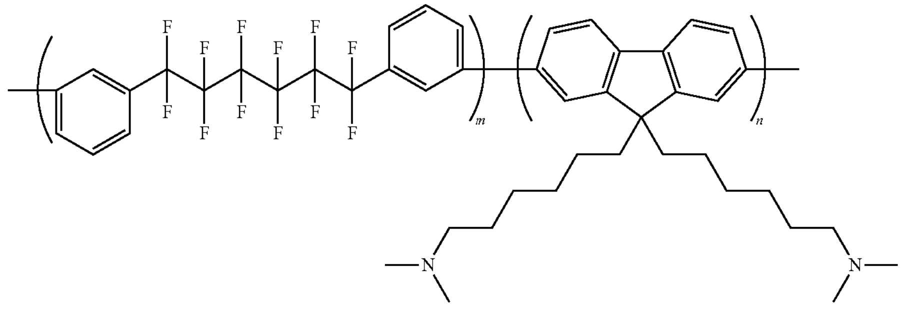

(Quaternization Reaction, Membrane Formation, and Ion Exchange)

To a 50 mL round-shaped three-necked flask were added the anion exchange resin precursor polymer 1 (1.70 g) and N,N-dimethylacetamide (9.6 mL). After the mixture was stirred to form a homogeneous solution, methyl iodide (0.45 mL, 7.22 mmol) was added, and the reaction was carried out at room temperature for 48 hours. N,N-dimethylacetamide (10 mL) was added to the reaction solution, and the solution was filtered. The filtrate was poured into a glass plate wound with silicone rubber and was kept on a hot plate adjusted so as to be oriented horizontally at 50° C. for drying. The resulting membrane was washed with pure water (2 L), and was then dried under vacuum overnight (60° C.) to obtain a transparent membrane having pale brown color. Further, the counter-ion of the anion exchange group (quaternary ammonium group) was converted from iodide ion to hydroxide ion by immersing it in 1 M aqueous potassium hydroxide solution for 48 hours and by washing it with degassed pure water. By the reaction, a membrane of an anion exchange resin represented by the following formula (m/n=1/0.30, hydroxide ion type) was obtained.

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 0.496 g, 3.14 mmol, 1.2 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 0.432 g, 1.57 mmol, 0.6 eq.), and the reaction was carried out at 80° C. for 1 hour. To the resulting slurry was added tetraethylammonium bromide (TEAB, 0.660 g, 3.14 mmol, 1.2 eq.) as a co-catalyst and zinc (Zn, 0.411 g, 6.28 mmol, 2.4 eq.) as a reducing agent, and the reaction was carried out at 80° C. for 2 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer 2 (yellow solid) represented by the following formula in a yield of 97%.

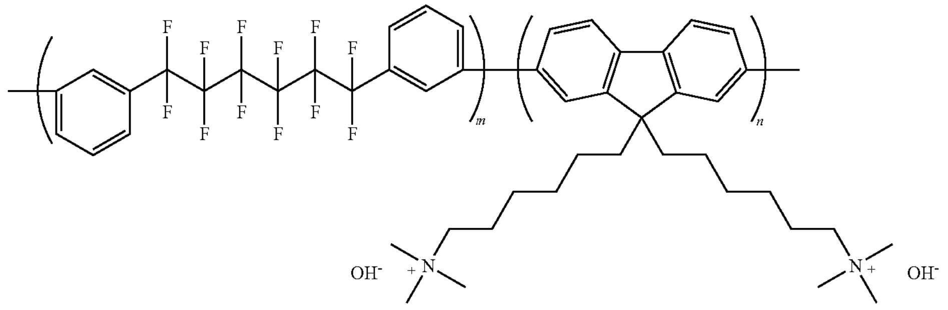

Example 2 Synthesis of Anion Exchange Resin 2

A membrane of an anion exchange resin 2 (m/n=1/0.30, hydroxide ion type) was obtained by a similar method of quaternization reaction, membrane formation, and ion exchange as in Example 1, except that an anion exchange resin precursor polymer 2 obtained by the following polymerization reaction was used.

Example 3 Synthesis of Anion Exchange Resin 3

A membrane of an anion exchange resin 3 (m/n=1/0.30, hydroxide ion type) was obtained by a similar method of quaternization reaction, membrane formation, and ion exchange as in Example 1, except that an anion exchange resin precursor polymer 3 obtained by the following polymerization reaction was used.

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 0.331 g, 2.10 mmol, 0.8 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 0.288 g, 1.05 mmol, 0.4 eq.), and the reaction was carried out at 80° C. for 1 hour. To the resulting slurry was added tetraethylammonium bromide (TEAB, 0.440 g, 2.10 mmol, 0.8 eq.) as a co-catalyst and zinc (Zn, 0.274 g, 4.19 mmol, 1.6 eq.) as a reducing agent, and the reaction was carried out at 80° C. for 2 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer 3 (yellow solid) represented by the following formula in a yield of 100%.

Example 4 Synthesis of Anion Exchange Resin 4

A membrane of an anion exchange resin 4 (m/n=1/0.30, hydroxide ion type) was obtained by a similar method of quaternization reaction, membrane formation, and ion exchange as in Example 1, except that an anion exchange resin precursor polymer 4 obtained by the following polymerization reaction was used.

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 0.248 g, 1.57 mmol, 0.6 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 0.216 g, 0.785 mmol, 0.3 eq.), and the reaction was carried out at 80° C. for 1 hour. To the resulting slurry was added tetraethylammonium bromide (TEAB, 0.330 g, 1.57 mmol, 0.6 eq.) as a co-catalyst and zinc (Zn, 0.206 g, 3.14 mmol, 1.2 eq.) as a reducing agent, and the reaction was carried out at 80° C. for 2 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer 4 (yellow solid) represented by the following formula in a yield of 100%.

Comparative Example 1: Synthesis of Anion Exchange Resin C1

A membrane of an anion exchange resin C1 (m/n=1/0.30, hydroxide ion type) was obtained by a similar method of quaternization reaction, membrane formation, and ion exchange as in Example 1, except that an anion exchange resin precursor polymer C1 obtained by the following polymerization reaction was used.

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 0.165 g, 1.05 mmol, 0.4 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 0.144 g, 0.52 mmol, 0.2 eq.), and the reaction was carried out at 80° C. for 1 hour. To the resulting slurry was added tetraethylammonium bromide (TEAB, 0.220 g, 1.05 mmol, 0.4 eq.) as a co-catalyst and zinc (Zn, 0.137 g, 2.09 mmol, 0.8 eq.) as a reducing agent, and the reaction was carried out at 80° C. for 2 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer 3 (yellow solid) represented by the following formula in a yield of 51%.

Comparative Example 2: Synthesis of Anion Exchange Resin C2

A membrane of an anion exchange resin C2 (m/n=1/0.30, hydroxide ion type) was obtained by a similar method of quaternization reaction, membrane formation, and ion exchange as in Example 1, except that an anion exchange resin precursor polymer C2 obtained by the following polymerization reaction was used.

(Polymerization Reaction)

To a 100 mL three-necked flask equipped with a nitrogen inlet and a condenser were added the monomer 1 (1.05 g, 2.01 mmol), the monomer 4 (0.295 g, 0.602 mmol), 2,2'-bipyridine (bpy, 1.984 g, 12.56 mmol, 4.8 eq.), and N,N-dimethylacetamide (6.3 mL). After the mixture was stirred to form a homogeneous solution, and the temperature was raised to 80° C. To the solution was added bis(1,5-cyclooctadiene)nickel(0) ($Ni(cod)_2$, 1.728 g, 6.28 mmol, 2.4 eq.), and the reaction was carried out at 80° C. for 3 hour. After the reaction mixture was naturally cooled to room temperature, the reaction was quenched by adding the reaction mixture dropwise to a mixed solution of methanol/pure water/12 M hydrochloric acid (1/1/2). The reaction mixture was filtered to collect the precipitate. The precipitate was washed with a mixed solution of methanol/pure water/12 M hydrochloric acid (1/1/2), with 0.2 M potassium carbonate, and with pure water, and was then dried under vacuum overnight (60° C.) to obtain an anion exchange resin precursor polymer C2 (yellow solid) represented by the following formula in a yield of 100%.

<Molecular Weight Evaluation>

The number average molecular weight Mn and the weight average molecular weight Mw of the anion exchange resin membranes obtained in the Examples and Comparative Examples were measured. The measurements were performed by gel permeation chromatography, in which Shodex K-805L was used as a column and polystyrenes were used as a standard material. The results are shown in TABLE 1.

TABLE 1

| | $Ni(cod)_2$/monomer | co-cat | Mn [kDa] | Mw [kDa] |
|---|---|---|---|---|
| Ex. 1 | 0.6 | TEAI | 9 | 81 |
| Ex. 2 | 0.6 | TEAB | 20 | 208 |
| Ex. 3 | 0.4 | TEAB | 18 | 150 |
| Ex. 4 | 0.3 | TEAB | 16 | 116 |
| Comp. Ex. 1 | 0.2 | TEAB | 4 | 7 |
| Comp. Ex. 2 | 2.4 | — | 16 | 136 |

The molecular weights (in particular, weight average molecular weights) of the Example samples are higher than the molecular weights (in particular, weight average molecular weights) of the Comparative Example samples, which indicates excellent mechanical property (strength).

What is claimed is:

1. A method for producing an anion exchange resin, comprising:

(A) preparing a monomer for forming a hydrophobic group, being composed of a single aromatic ring or being composed of a plurality of aromatic rings which are connected to each other via a divalent hydrocarbon group, a divalent silicon-containing group, a divalent nitrogen-containing group, a divalent phosphorus-containing group, a divalent oxygen-containing group, a divalent sulfur-containing group, or direct bond, wherein two chlorine atoms are bonded to the single aromatic ring, or to each of two terminal aromatic rings of the plurality of aromatic rings;

(B) preparing a monomer for forming a hydrophilic group, being composed of a single aromatic ring or being composed of a plurality of aromatic rings which are connected to each other via a linking group and/or via direct bond; wherein the linking group is a divalent hydrocarbon group, a divalent silicon-containing group, a divalent nitrogen-containing group, a divalent phosphorus-containing group, a divalent oxygen-containing group, or a divalent sulfur-containing group; two chlorine atoms are bonded to the single aromatic ring or to each of the two terminal aromatic rings of the plurality of aromatic rings; and at least one of the linking group or the aromatic ring of the single aromatic ring or the plurality of aromatic rings is connected to a precursor functional group for an anion exchange group via a divalent saturated hydrocarbon group or direct bond;

(C) reacting the monomer for forming a hydrophobic group with the monomer for forming a hydrophilic group in the presence of bis(1,5-cyclooctadiene)nickel (0) as a catalyst, 2,2'-bipyridine as a co-ligand, a bromide or an iodide as a co-catalyst, and a reducing agent to synthesize a polymer; and (D) producing an anion exchange group by ionizing the precursor functional group to form the anion exchange resin;

wherein a mole number of bis(1,5-cyclooctadiene)nickel (0) used in the step (C) is 0.3 to 1.8 times a total mole number of the monomer for forming a hydrophobic group and the monomer for forming a hydrophilic group; and wherein, in the anion exchange resin, a residue of the monomer for forming a hydrophobic group forms a divalent hydrophobic group; a residue of the monomer for forming a hydrophilic group having the anion exchange group forms a divalent hydrophilic group; and the hydrophobic group is connected to the hydrophilic group via direct bond.

2. The method for producing an anion exchange resin according to claim 1, wherein the co-catalyst is a quaternary ammonium bromide or a quaternary ammonium iodide.

3. The method for producing an anion exchange resin according to claim 1, wherein a mole number of the co-catalyst used in the step (C) is 1.0 to 3.0 times a mole number of bis(1,5-cyclooctadiene)nickel(0).

4. The method for producing an anion exchange resin according to claim 1, wherein the reducing agent is metallic zinc or metallic magnesium.

5. The method for producing an anion exchange resin according to claim 1, wherein a mole number of 2,2'-bipyridine used in the step (C) is 1.5 to 2.5 times the mole number of bis(1,5-cyclooctadiene)nickel(0).

6. The method for producing an anion exchange resin according to claim 1, wherein the hydrophobic group comprises a bisphenol residue which may be substituted with a halogen atom, a pseudohalide, an alkyl group, or an aryl group, represented by the following formula (2):

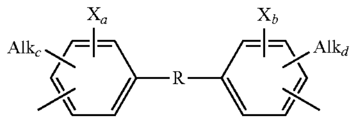

(2)

wherein, in the formula, R represents a divalent hydrocarbon group, a divalent silicon-containing group, a divalent nitrogen-containing group, a divalent phosphorus-containing group, a divalent oxygen-containing group, a divalent sulfur-containing group, or direct bond, which may be substituted with a halogen atom or a pseudohalide; Alk are the same or different from each other and each represents an alkyl group or an aryl group; X are the same or different from each other and each represents a halogen atom or a pseudohalide; and a, b, c, and d are the same or different from each other and each represents an integer of 0 to 4.

7. The method for producing an anion exchange resin according to claim 6, wherein the hydrophobic group comprises a bisphenol residue which may be substituted with a halogen atom, a pseudohalide, an alkyl group, or an aryl group, represented by the following formula (1):

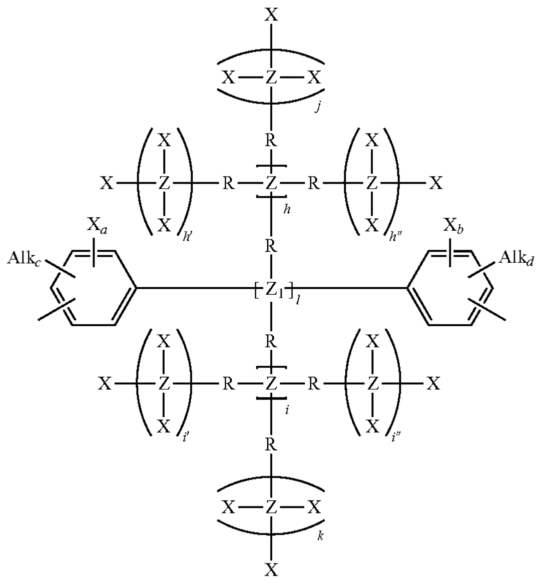

(1)

wherein, in formula (1), Alk, X, a, b, c, and d have the same meaning as Alk, X, a, b, c, and d, respectively, in the formula (2); Z are the same or different from each other and each represents carbon atom or silicon atom; R are the same or different from each other and each represents a divalent silicon-containing group, a divalent nitrogen-containing group, a divalent phosphorus-containing group, a divalent oxygen-containing group, a divalent sulfur-containing group, or direct bond; l represents an integer of 1 or more; and h, h', h", i, i', i", j, and k are the same or different from each other and each represents an integer of 0 or more.

8. The method for producing an anion exchange resin according to claim 7, wherein, in the above formula (1), Z is a carbon atom, R is a direct bond, X is fluorine atom, and h, h', h", i, i', i", j, and k are 0.

9. The method for producing an anion exchange resin according to claim 1, wherein the hydrophilic group is a divalent hydrophilic group, being composed of a single polycyclic compound or being composed of a plurality of polycyclic compounds which are connected to each other via a linking group and/or via direct bond; wherein the linking group is a divalent hydrocarbon group, a divalent silicon-containing group, a divalent nitrogen-containing group, a divalent phosphorus-containing group, a divalent oxygen-containing group, or a divalent sulfur-containing group; and at least one of the linking group or the polycyclic compound is connected to an anion exchange group via a divalent saturated hydrocarbon group with a carbon number of 2 or more.

10. The method for producing an anion exchange resin according to claim 9, wherein the hydrophilic group comprises a fluorene residue represented by the following formula (3):

(3)

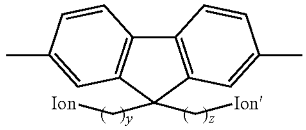

wherein, in the formula, Ion and Ion' are the same or different from each other and each represents an anion exchange group, and y and z are the same or different from each other and each represents an integer of 2 to 20.

11. A method for producing an electrolyte membrane, comprising:

obtaining an anion exchange resin produced by the method of claim 1;

casting the anion exchange resin to form a membrane thereof; and immersing the membrane in an aqueous solution of potassium hydroxide to convert the anion exchange resin into a hydroxide form to obtain an electrolyte membrane.

* * * * *